United States Patent [19]

Heiliger

[11] Patent Number: 5,171,231
[45] Date of Patent: Dec. 15, 1992

[54] SAFELY DISPOSABLE CANNULA ASSEMBLY

[75] Inventor: Raymund Heiliger, Herzogenrath, Fed. Rep. of Germany

[73] Assignee: Vygon GMBH & Co. KG, Herzogenrath, Fed. Rep. of Germany

[21] Appl. No.: 663,389

[22] Filed: Mar. 4, 1991

[30] Foreign Application Priority Data

Mar. 16, 1990 [DE] Fed. Rep. of Germany ....... 4008392

[51] Int. Cl.⁵ .............................................. A61M 5/00
[52] U.S. Cl. .................................... 604/263; 604/164; 604/192; 604/167
[58] Field of Search ............... 604/110, 263, 264, 280, 604/192, 197, 198, 164, 167, 171

[56] References Cited

U.S. PATENT DOCUMENTS

| | | | |
|---|---|---|---|
| 4,810,248 | 3/1989 | Masters et al. | 604/192 |
| 4,828,548 | 5/1989 | Walter | 604/167 |
| 4,842,586 | 6/1989 | Hogan | 605/198 |
| 4,850,961 | 7/1989 | Wanderer et al. | 604/263 |
| 4,917,669 | 4/1990 | Bonaldo | 604/198 |
| 4,994,045 | 2/1991 | Ranford | 604/263 |
| 5,030,212 | 7/1991 | Rose | 604/263 |

FOREIGN PATENT DOCUMENTS 2625103 6/1989 France ................. 604/198

Primary Examiner—C. Fred Rosenbaum
Assistant Examiner—Chalin Smith
Attorney, Agent, or Firm—Mark T. Basseches

[57] ABSTRACT

A cannula assembly provides for secure protection of the cannula prior to use and safe disposal after use. A tubular resilient sleeve includes a longitudinal slot. The cannular includes a radial projection which, after use of the cannula, may be inserted within the slot and slid interiorly of the sleeve to lock the cannula in protected position. A cannula shield includes an adapter insertible into the slotted end of the sleeve to spread the slot and facilitate insertion of the cannula into the slot.

3 Claims, 1 Drawing Sheet

SAFELY DISPOSABLE CANNULA ASSEMBLY

BACKGROUND OF THE INVENTION

This invention relates to safely disposable cannula device or receptacle including a protective sleeve provided with a longitudinal slot to house a steel cannula. The cannula is provided at its proximal end with an adapter on which a radially protruding actuating element is integrally formed.

THE PRIOR ART

The purpose of such devices is in particular sanitary protection before use and the safe disposal of used steel cannulas which, depending on their contamination having occurred in use, may be a considerable source of infection.

A known cannula receptacle device consists of a box-like protective sleeve of rectangular cross-section, which is provided with a longitudinal slot which extends to a distance before the entry end of the protective sleeve A slide, also box-like, surrounds the protective sleeve and is displaceable between two end positions by stops integrally formed on the protective sleeve. A web integrally formed inside the slide points through the slot into the box-like sleeve and is in one piece with the adapter of the steel cannula. As the slide is being moved relative to the sleeve in the longitudinal direction thereof, the steel cannula thus rigidly connected with the slide penetrates more and more into the sleeve until the steel cannula is completely inside the sleeve in a fixable end position.

With the known receptacle device it is possible to ensure safe disposal of a used steel cannula. The protective sleeve provided for this purpose and in particular the slide made in one piece with the adapter of the steel cannula requires complicated forms for molding these parts and considerably increases the total cost of the device.

SUMMARY OF THE INVENTION

It is an object of the invention to provide a cannula assembly which not only is cost-effective to manufacture but also is usable for conventional steel cannulas without its adapter having to be equipped with specially designed actuating means for transferring the steel cannula into the receptacle device.

For the solution of the problem there is provided a tubular resilient plastic protective sleeve which encompasses the cannula prior to use. A longitudinal slot is formed in the sleeve part way toward the other end, the slot in the normal or unstressed condition of the sleeve being closed or of a narrow transverse extent. An adapter piece forming a cannula shield prior to use is frictionally mounted in the other (unslotted) end of the sleeve. A steel cannula is axially housed in the cannula shield prior to use and includes a head portion connected to a radially extending gripper plate portion by a narrow link.

After the cannula is used it may be safely and non-removably stored in the sleeve. This is accomplished by inserting the adapter piece of the cannula shield into the slotted end of the sleeve with resultant spreading of the slot. The cannula may now be inserted in a radial direction into the sleeve through the spread slot and slid longitudinally until the entire cannula is encompassed within the sleeve. Preferably, the cannula is shifted inwardly until the link is aligned with an enlargement of the slot.

With the parts thus positioned the adapter is removed from the sleeve permitting the slot to narrow capturing the cannula between the walls forming the edges of the slot in the sleeve. Where the slot includes an enlargement the link of the cannula is locked in the enlargement when the slot narrows, securely locking the cannula in the sleeve. The sleeve and cannula may now be safely discarded.

In order not to have to rely solely on the widening of the slot by the clamping of the protective sleeve onto the adapter piece of the plastic cannula, to facilitate introduction of the actuating element into the slot, a variant of the invention proposes enlarging the slot at the end of the protective sleeve by triangular cutouts in the sleeve wall.

The device according to the invention is not only suitable for the safe accommodation of used steel cannula, but is eminently suitable also to serve as protective device for a cannula set consisting of steel cannula and a plastic cannula, until the set is used. For this purpose, a further variant of the invention provides that the inside diameter of the protective sleeve is adapted at its unslotted end to frictionally receive the outside diameter of a cylindrical adapter part of the plastic cannula slipped onto the steel cannula, which (part) faces the distal end of the plastic cannula.

BRIEF DESCRIPTION OF THE DRAWINGS

A practical example of a device according to the invention is illustrated in the drawings.

DETAILED DESCRIPTION OF DRAWINGS

Figure 1:
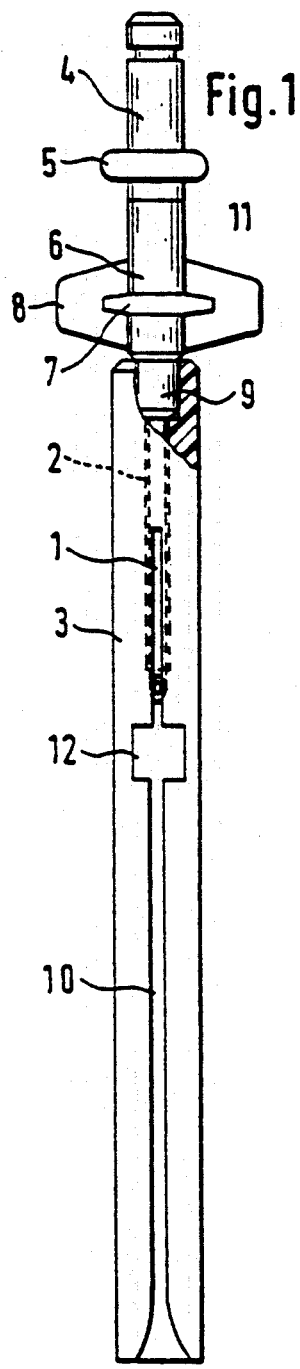
FIG. 1 shows a cannula assembly in accordance with the invention prior to use.

As shown in FIG. 1, a steel cannula 1 and a plastic cannula shield 2 slipped onto it are lodged in a cylindrical protective sleeve 3. An essentially cylindrical proximal adapter 4 of the steel cannula 1, provided with a radially extending grip plate 5, remains outside the protective sleeve 3, as does also the major part of an adapter 6 of the plastic shield 2, which is likewise provided with a radially extending grip plate 7 and with a tangentially disposed attachment wing 8. Adapter 6 protrudes into the protective sleeve 3 only by a segment 9. The outside diameter of segment 9 is adapted to the inside diameter of the protective sleeve 3 made of elastically deformable plastic, in such a way that a clamping fit is obtained. In this state the parts form a compact sales unit which can be packed aseptically in the conventional manner.

Figure 2:
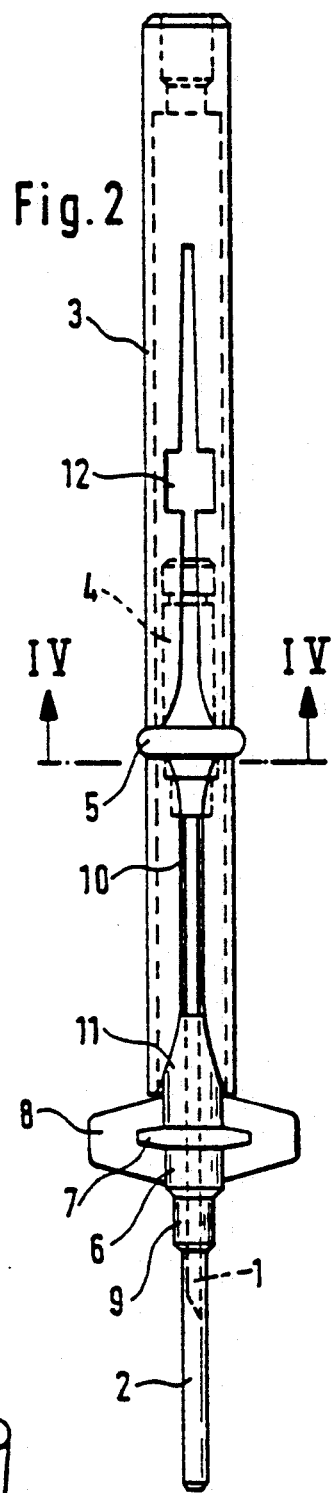
FIG. 2 is a view similar to FIG. 1 with the used cannula partially shifted toward its disposal position in the sleeve.
Figure 3:
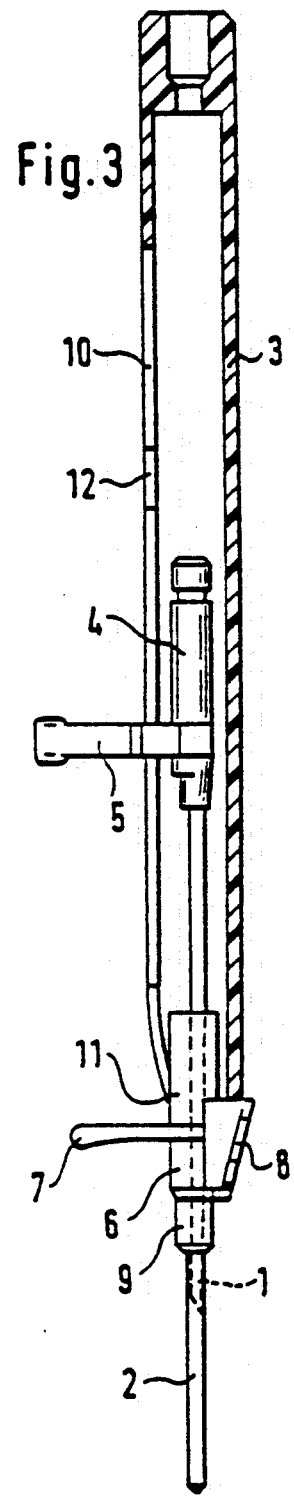
FIG. 3 is a view similar to FIG. 2 showing the parts in longitudinal sections.
Figure 4:
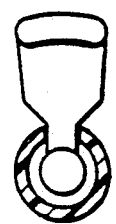
FIG. 4 is a section taken on line IV—IV of FIG. 2.

According to the representations in FIG. 2 and 3, after use of the steel cannula the protective sleeve 3 serves as a receptacle, so as to permit its disposal without danger of being hurt or infected by the steel cannula.

To this end, the protective sleeve 3 is provided with a longitudinal slot 10 which extends to the end of the protective sleeve 3, which as shown in FIG. 1, points away from the cannulas 1 and 2. The lead end of the slot 10 is preferably provided with a widened area 10a forming cam surfaces. As shown in FIG. 2 and 3 a cylindrical adapter piece 11 of the plastic cannula shield 2 has been inserted into the slotted end of the sleeve 3. The longitudinal slot 10 is widened by the spreading force of portion 11, so that a connecting region or link 13 between the grip plate 5 and the adapter 4 of the steel cannula can be introduced effortlessly into the widened longitudinal slot 10. Under temporary expansion of the longitudinal slot 10, which in the unstressed condition is normally almost closed, the steel cannula 1 can then be drawn into the protective sleeve with the aid of the grip plate 5, until the connecting region 13 between the grip plate 5 and the adapter 4 of the steel cannula 1 snaps into a step-like enlargement 12 of the longitudinal slot 10. Then, due to the elasticity of the plastic material of which the protective sleeve 3 is made, the longitudinal slot 10 assumes its original width and prevents a redisplacement of the steel cannula 1.

Insertion of the cannula link 13 into slot 10 and the adapter piece 11 into the slot is facilitated by the cam surfaces at 10a.

Naturally, the enlargement 12 is situated so that the steel cannula 1 is completely enclosed by the protective sleeve 3 at the latest when the grip plate 5 has reached the enlargement 12. The protective sleeve 3 can then be pulled off the adapter piece 11 of the plastic cannula 2 and be disposed of safely with the steel cannula 1.

The device of the invention provides a readily manufactured inexpensive and effective safely disposable cannula assembly. As will be evident to workers skilled in the art and familiarized with the instant disclosure, numerous variations in details of construction may be made without departing from the spirit of the invention which is to be broadly construed within the scope of the appended claims.

I claim:

1. A safety disposable cannular assembly comprising an elongate resilient tubular sleeve, a longitudinal slot extending from a first end of said sleeve and terminating short of the other end of said sleeve, a polymeric cannula shield member including a neck portion frictionally mounted in said other end of said sleeve, said shield member including a cannula receiver portion disposed within said sleeve, a cannula member removeably mounted within said shield member and including a head portion extending axially outwardly beyond said other end of said sleeve, a grip plate extending radially outwardly from said heat portion and a radially directed connector link interposed between said plate and said head portion, the transverse dimension of said link being greater than the transverse dimension of said slot in the unstressed condition of said sleeve, said neck portion of said shield being insertable into said first end of said sleeve and being sized, when so inserted to expand said slot in a transverse direction whereby said link of said cannula member may be axially shifted within said slot.

2. A cannula assembly in accordance with claim 1 and including an enlargement portion formed in said slot at a position remote from said first end of said shield, the transverse dimension of said enlargement portion being greater than the transverse dimension of said link.

3. A cannula assembly in accordance with claim 2 and including cam means formed on said first end of said sleeve in communication with said slot, said cam means being positioned to coact with said link for transversely spreading said slot responsive to longitudinal movements of said link against said cam means in the direction from said first end toward said other end.

* * * * *